United States Patent
Birkhold et al.

(10) Patent No.: US 12,106,449 B2
(45) Date of Patent: Oct. 1, 2024

(54) SPATIOTEMPORAL FUSION OF TIME-RESOLVED ANGIOGRAPHIC DATA SETS

(71) Applicant: Siemens Healthineers AG, Forccheim (DE)

(72) Inventors: Annette Birkhold, Stuttgart (DE); Markus Kowarschik, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/230,790

(22) Filed: Aug. 7, 2023

(65) Prior Publication Data

US 2024/0062340 A1 Feb. 22, 2024

(30) Foreign Application Priority Data

Aug. 22, 2022 (DE) .................... 10 2022 208 655.4

(51) Int. Cl.
*G06T 5/50* (2006.01)
*A61B 6/00* (2024.01)
(Continued)

(52) U.S. Cl.
CPC ............... *G06T 5/50* (2013.01); *A61B 6/481* (2013.01); *A61B 6/504* (2013.01); *G06T 7/0016* (2013.01);
(Continued)

(58) Field of Classification Search
CPC ......... G06T 5/50; G06T 7/0016; G06T 15/00; G06T 2200/04; G06T 2207/20221;
(Continued)

(56) References Cited

U.S. PATENT DOCUMENTS

2011/0037761 A1 2/2011 Mistretta et al.
2012/0020462 A1 1/2012 Grass et al.
(Continued)

FOREIGN PATENT DOCUMENTS

CN 102696056 A 9/2012
CN 110349175 A 10/2019
(Continued)

OTHER PUBLICATIONS

Chen, K-K., et al. "Application of time-resolved 3D digital subtraction angiography to plan cerebral arteriovenous malformation radiosurgery." American Journal of Neuroradiology 38.4 (2017): 740-746.
(Continued)

*Primary Examiner* — Siamak Harandi
(74) *Attorney, Agent, or Firm* — Lempia Summerfield Katz LLC

(57) ABSTRACT

Angiographic recordings are to be made more informative. To this end, a method for spatiotemporal fusion of time-resolved angiographic data sets is proposed. Respective 4D reconstructions are obtained from angiographic 3D data sets acquired from contrast agents administered at different sites. In both 4D reconstructions, a common vascular region is identified. For each contrast agent bolus, the corresponding time point or time course in the common vascular region is determined. Finally, the two 4D reconstructions are synchronized and fused.

17 Claims, 3 Drawing Sheets

(51) Int. Cl.
*A61B 6/50* (2024.01)
*G06T 7/00* (2017.01)
*G06T 15/00* (2011.01)

(52) U.S. Cl.
CPC .......... *G06T 15/00* (2013.01); *G06T 2200/04* (2013.01); *G06T 2207/20221* (2013.01); *G06T 2207/30048* (2013.01); *G06T 2207/30104* (2013.01)

(58) Field of Classification Search
CPC . G06T 2207/30048; G06T 2207/30104; A61B 6/481; A61B 6/504; A61B 5/0035; A61B 5/0042; A61B 5/5217; A61B 6/5235; A61B 6/032; A61B 5/055; G06V 20/69; G16H 30/20
See application file for complete search history.

(56) References Cited

U.S. PATENT DOCUMENTS

| | | |
|---|---|---|
| 2018/0199905 A1 | 7/2018 | Kowarschik et al. |
| 2018/0218521 A1* | 8/2018 | Kowarschik .......... G06T 11/008 |
| 2021/0090256 A1 | 3/2021 | Kowarschik |
| 2023/0102646 A1 | 3/2023 | Birkhold et al. |

FOREIGN PATENT DOCUMENTS

| | | |
|---|---|---|
| CN | 112617867 A | 4/2021 |
| DE | 102017200489 A1 | 7/2018 |
| DE | 102021210879 A1 | 3/2023 |
| WO | 2015044433 A1 | 4/2015 |

OTHER PUBLICATIONS

Copeland, Andrew et al., "Spatio-Temporal Data Fusion for 3D+T Image Reconstruction in Cerebral Angiography," EEE Transactions on Medical Imaging; vol. 29; No. 6; pp. 1238-1251; 2010.

* cited by examiner

SPATIOTEMPORAL FUSION OF TIME-RESOLVED ANGIOGRAPHIC DATA SETS

The present patent document claims the benefit of German Patent Application No. 10 2022 208 655.4, filed Aug. 22, 2022, which is hereby incorporated by reference in its entirety.

TECHNICAL FIELD

The present disclosure relates to a method for spatiotemporal fusion of time-resolved angiographic data sets. The present disclosure also relates to a corresponding image processing apparatus and an angiography apparatus. The present disclosure further relates to a computer program and an electronically readable data carrier.

BACKGROUND

So-called AVMs (arteriovenous malformations) may constitute tangles of vessels in the brain of a patient and may be supplied with blood via a plurality of large arteries. AVFs (arteriovenous fistulas) may be thought of as "short circuits" between arteries and veins that may be difficult to locate and detect. In addition, venous outflow may occur in a combined manner due to so-called shunts, i.e., there is not just one, but a plurality of outflows.

In order to achieve a better understanding of the flow conditions in an AVM having two inflows, the inflows with their respective effects on the vascular system as a whole are nowadays examined separately. For this purpose, for example, two separate 3D DSA recordings or 4D DSA recordings (DSA: digital subtraction angiography) or similar recordings are obtained. For the first recording, a contrast agent is injected into the first inflow. Also, for the second recording, a contrast agent is injected into the second inflow. The two recordings are then spatially fused.

Such fusion of 3D or 4D DSA recordings is demonstrated in K.-K. Chen at al: "Application of time resolved 3D digital subtraction angiography to plan cerebral arteriovenous malformation radio surgery," Jan. 26, 2017, 10.3174/ajnr.A5074. The 4D sequence of one of the data sets may be shown in a time-dependent manner, while the second data set is only rendered statically.

SUMMARY AND DESCRIPTION

The object of the present disclosure is therefore to improve the rendering of a complex vascular system.

This object is achieved by a method, an image processing apparatus, an angiography apparatus, a corresponding computer program, and a data carrier as described herein.

The scope of the present disclosure is defined solely by the appended claims and is not affected to any degree by the statements within this summary. The present embodiments may obviate one or more of the drawbacks or limitations in the related art.

In order to assess the overall pathology of, for example, an AVM, an image containing all the relevant 4D flow information (moving 3D images or 3D videos) in combined form would provide better understanding of the AVM architecture and thus facilitate treatment planning. For example, the 4D flow data may be acquired using an X-ray-based medical imaging modality such as an X-ray angiography system or a CT scanner. Also, magnetic resonance imaging (MRI) permits the recording of such 4D images. In addition, combined visualization of all the relevant structures of all the 3D and/or 4D recordings may be helpful during treatment.

A method for spatiotemporal fusion of time-resolved angiographic data sets is provided for this purpose. Thus, two or more time-resolved angiographic data sets are available that are fused not only spatially but also temporally.

A first time-resolved angiographic 3D data set of a patient who has received a first administration of contrast agent at a first site is initially provided. It may be provided by making the 3D data set available in a storage unit of a computer via a cloud or via the Internet, or by some other data carrier. Alternatively, it may be provided directly by an angiography unit that obtains or acquires the respective time-resolved angiographic 3D data set of the patient. This first data set should represent a recording of the patient after the latter has received an administration of contrast agent at a first site, for example, a first inflow of the AVM. The contrast agent then spreads out from the first inflow into the AVM or tangle of blood vessels.

Similarly, a second time-resolved angiographic 3D data set of the patient who has received a second administration of contrast agent at a second site different from the first is provided. Like the provision of the first data set, the second data set may be provided in the various ways mentioned above. The second contrast agent administration takes place at a second site, such as a second inflow to the AVM, which is different from the first site. This enables the effects of both inflows to be analyzed.

A first 4D reconstruction is then obtained from the first time-resolved angiographic 3D data set. A 4D reconstruction with three spatial dimensions and one temporal dimension is obtained from the 3D recordings recorded consecutively over time (three spatial dimensions). This 4D reconstruction is, for example, a spatial video recording showing the spreading of the contrast agent in the vascular system under examination. Similarly, a second 4D reconstruction is also obtained from the second time-resolved angiographic 3D data set. This provides, for example, two video recordings of the two different contrast agent injections into the vascular system.

In a further act, a common vascular region represented by the two 4D reconstructions is determined, wherein the vascular region originates from the patient, i.e., represents part of their vascular system. This common vascular region, which is thus imaged in both recordings, is determined in the 4D reconstructions. For example, if it is the AVM with the two inflows, and contrast agent was applied to the two different inflows, the common vascular region represents a vascular region that is jointly supplied by both inflows.

A first time point or first time course relating to an appearance of a first contrast agent bolus of the first contrast agent administration in the common vascular region is then determined from the first 4D reconstruction. The quantity of contrast agent injected during the first contrast agent administration, e.g., the contrast agent bolus (bolus for short), is transported from the first site to the common vascular region. This occurs at a particular speed, wherein the blood flowing in the vessels dilutes the contrast agent. The contrast agent delivered with the injection therefore appears in a downstream vascular region over a certain time course (time-contrast curve). The contrast agent concentration gradually increases and decreases again after the injection (which is longer for tomographic imaging). This variation over time in the concentration of the contrast agent at a vascular point or in a vascular region is referred to here as the appearance of the contrast agent bolus in the (common)

vascular region. With respect to this "appearance," a time point or the entire time course of the contrast agent concentration may be determined. For example, the determined time point may be the time of arrival of the bolus in the common vascular region.

Similarly, a second time point or second time course relating to an appearance of a second contrast agent bolus of the second contrast agent administration in the common vascular region is determined from the second 4D reconstruction. Again, for example, the time of arrival of the second bolus in the common vascular region may be determined.

Following this, the first 4D reconstruction and the second 4D reconstruction may be synchronized based on the first and second time points or time courses. For example, if the first and second time points are each the time of arrival of the respective bolus in the common vascular region, these two times of arrival may be used to synchronize the 4D reconstructions or videos. Thus, for example, after synchronization, the two contrast agent boluses arrive in the common vascular region at the same point in time.

Finally, the two synchronized 4D reconstructions are fused. Fusion means that the 4D reconstructions are superimposed in a spatially correct manner. Because the 4D reconstructions are also synchronized to each other, fusing is equivalent to 4D fusion. This means that in the fused 4D reconstruction or video, there is not only spatial merging, but also temporal merging of the individual reconstructions or videos. In other words, an approach is proposed for spatially and temporally fusing two (or more) angiographic 4D data sets to produce a single time-synchronized combined 4D data set.

For example, because of the underlying blood flow dynamics, angiographic 4D images may be temporally registered by identifying vascular regions (e.g., individual voxels or regions of voxels) that are contrast-enhanced in both (all) 4D data sets. Separate identification of the time points at which these common regions are contrast-enhanced in both (all) 4D images allows temporal synchronization of the data sets.

In one embodiment of the method, the first and second time points each correspond to an arrival time of the respective contrast agent bolus in the common vascular region. The vascular region may be selected larger or smaller. For example, the vascular region may include a tangle of vessels or only a single vessel. The respective arrival location is monitored by image processing. For example, a blackening in the vascular region is detectable when the contrast agent arrives in the vascular region. With respect to the blackening, a single vessel may thus be monitored, for example, or averaging over a larger vessel area may be performed. As mentioned above, the concentration of the contrast agent in the vascular region initially increases continuously and reaches a peak. As the contrast agent flows downstream, the concentration continuously decreases again. If the concentration or blackening exceeds a detection threshold, for example, this may be defined as the arrival time of the contrast agent bolus. In this way, the arrival time for the bolus of the first contrast agent administration and the bolus of the second contrast agent administration may be determined in each case. The first time point and the second time point thus obtained may then be equated for synchronization.

In an alternative embodiment of the method, the first time point and the second time point each correspond to a time of maximum concentration of the respective contrast agent bolus in the common vascular region. Because the contrast agent concentration has a certain time course, a defined time point may be selected from this time course that is representative of the progression. In the present case, the concentration peak is used to determine the representative time point for the concentration profile. Such a peak may be reliably determined by image processing.

In a further alternative of the method, the first and the second time point each correspond to a time point when a respective center of gravity of the respective contrast agent bolus resides in the common vascular region. The center of gravity of the respective contrast agent bolus may be determined, for example, from the time course of a relatively short contrast agent bolus. For example, the center of gravity of the respective contrast agent bolus may be defined as the center of gravity of the respective flow function of the contrast agent bolus in the particular vascular region. This center of gravity may also be determined automatically by functional analysis of the contrast agent flow behavior.

In a further exemplary embodiment, a time point of maximum cross-correlation of the first and second time course (possibly with contrast agent inflow and outflow or inflow only in each case) is used for synchronization. Here, a respective time point is not therefore determined directly from each individual time course, but the time courses of both contrast agent administrations are directly subject to cross-correlation or the like. Thus, the entire time course of each contrast agent bolus is used to perform the synchronization. Figuratively speaking, the two time courses are superimposed in such a way that they have the greatest possible correspondence. Thus, not only a single time point for each bolus, but the entire respective time course is used for synchronization.

According to another exemplary embodiment, a plurality of vascular regions are determined from the 4D reconstructions into which both the first and second contrast agent boluses flow, and the vascular region that is reached first by the respective contrast agent bolus of the two contrast agent administrations is automatically determined as the common vascular region. The contrast agent from the first contrast agent injection and the second contrast agent injection may flow into a plurality of common vascular regions. Because the contrast agent becomes increasingly diluted over time, it is advantageous to select the earliest possible time point for synchronization. For synchronization, it is therefore advantageous to use the first common vascular region into which the contrast agent of both the first contrast agent administration and the second contrast agent administration flows. The contrast agent may be best detected, in particular, identified in each case in this first common vascular region.

In another exemplary embodiment, at least one further 4D reconstruction is synchronized and fused with the first and second 4D reconstructions. Thus, for example, not only two video recordings but three or more video recordings are synchronized and fused with one another. Relevant data sets may be obtained using different imaging modalities (angiography system, CT scanner, etc.). This allows significantly better analysis of a highly complex vascular system.

In addition, in an exemplary embodiment, the first and second 4D reconstructions may be fused with an angiographic 3D data set. In this way, for example, two video recordings from a smaller vascular region may be projected or embedded in a static overall vascular structure. This allows the treating physician to better plan a therapy, for example, if the physician sees the area to be treated in a larger vascular tree or an overall vascular tree.

In addition, in an exemplary embodiment, the first and second 4D reconstructions may be fused with a 3D tomographic data set. For example, the 3D tomographic data set provides a detailed representation of the patient's anatomy. The vascular regions represented by the two 4D reconstructions may thus be accurately fitted into the patient's spatial anatomy. This type of fused representation also helps the planning or treating physician to better assess the vascular situation.

The above-mentioned object is also achieved by an image processing apparatus for spatiotemporal fusion of time-resolved angiographic data sets. The image processing apparatus includes a storage unit configured to: provide a first time-resolved angiographic 3D data set for a patient who has received a first contrast agent administration at a first site; and provide a second time-resolved angiographic 3D data set for the patient who has received a second contrast agent administration at a second site different from the first site. The image processing apparatus further includes an image processing unit configured to: obtain a first 4D reconstruction from the first time-resolved angiographic 3D data set; obtain a second 4D reconstruction from the second time-resolved angiographic 3D data set; determine a common vascular region represented by both 4D reconstructions of the patient; determine a first time point or time course relating to an appearance of a first contrast agent bolus of the first contrast administration in the common vascular region from the first 4D reconstruction; determine a second time point or time course relating to an appearance of a second contrast bolus of the second contrast agent administration in the common vascular region from the second 4D reconstruction; synchronize the first 4D reconstruction and the second 4D reconstruction on the basis of the first and second time points or time courses; and fuse the two synchronized 4D reconstructions.

The image processing apparatus is therefore capable of synchronizing and fusing angiographic 4D reconstructions according to the above method. The advantages and developments described above in connection with the method apply mutatis mutandis to the image processing apparatus. In this context, the respective process acts may be seen as functional features of corresponding units of the image processing apparatus.

In addition, an angiography apparatus for spatiotemporal fusion of time-resolved angiographic data sets is provided. The angiography apparatus includes an angiography unit configured to: acquire a first time-resolved angiographic 3D data set for a patient who has received a first contrast agent administration at a first site; and acquire a second time-resolved angiographic 3D data set for the patient who has received a second contrast agent administration at a second site different from the first. The angiography apparatus further includes an image processing unit configured to: obtain a first 4D reconstruction from the first time-resolved angiographic 3D data set; obtain a second 4D reconstruction from the second time-resolved angiographic 3D data set; determine a common vascular region represented by both 4D reconstructions of the patient; determine a first time point or time course relating to an appearance of a first contrast agent bolus of the first contrast administration in the common vascular region from the first 4D reconstruction; determine a second time point or time course regarding an appearance of a second contrast agent bolus of the second contrast administration in the common vascular region from the second 4D reconstruction; synchronize the first 4D reconstruction and the second 4D reconstruction based on the first and second time points or time courses; and fuse the two synchronized 4D reconstructions.

Here, the angiography apparatus is capable of generating the angiographic 3D data sets itself. The angiography apparatus may also have a storage facility for temporarily storing the acquired angiographic 3D data sets. However, this storage unit need not be explicitly present.

With respect to developments and advantages of the angiography apparatus, the above comments in connection with the image processing apparatus apply.

According to another aspect, a computer program including instructions is provided. When the instructions are executed by at least one image processing apparatus of the above type, the instructions cause the image processing apparatus to perform a method as described herein. The instructions may be in the form of program code. The program code may be provided as binary code or assembler and/or as source code of a programming language, (e.g., C), and/or as a program script, (e.g., Python).

In addition, an electronically readable data carrier on which the described computer program is stored is also provided here. The data carrier may be a DVD, a memory stick, or similar.

BRIEF DESCRIPTION OF THE DRAWINGS

The disclosure is now be explained in more detail with reference to the accompanying drawings in which.

DETAILED DESCRIPTION

Figure 1:
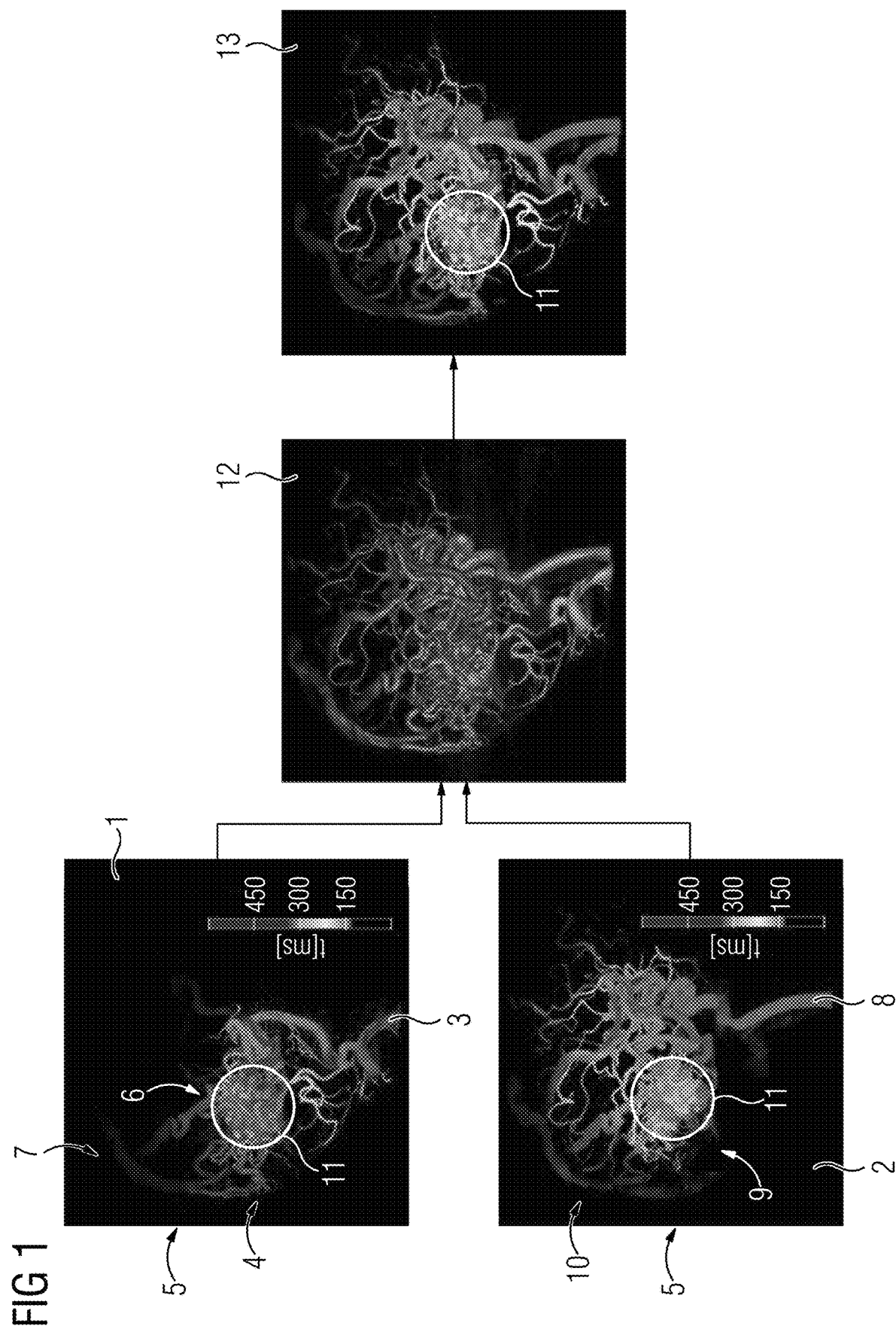
FIG. 1 depicts an example of a schematic sequence of a spatiotemporal fusion of two angiographic 4D data sets.

The exemplary embodiments described in more detail below represent embodiments of the present disclosure. In the figures, identical or functionally identical elements may be provided with the same reference characters. The description of identical or functionally identical elements may not necessarily be repeated in respect of different figures.

If, in the context of the present disclosure, reference is made to the fact that a component of the image processing apparatus or angiography apparatus or the image processing unit thereof is set up, configured, designed or the like to perform or implement a specific function, to achieve a specific effect or to serve a specific purpose, this may be understood as meaning that, by corresponding adaptation, programming, physical design and so on, the component is concretely and actually capable of executing or realizing the function, achieving the effect or serving the purpose, over and above the principle or theoretical usability or suitability of the component for this function, effect or purpose.

In an embodiment, the following acts may be performed, among others: (1) recording of two or more contrast-enhanced 3D data sets of the patient using different contrast agent injection sites (e.g., different arterial inflows of a diseased vascular region, such as in the patient's brain); (2) 4D reconstruction of the angiographic data sets (for example, using a flow restriction based approach, such as described in DE 10 2017 200 489 A1); (3) determining the temporal dynamics for each vascular voxel (or region of vascular voxels) in the reconstructed 4D images (for example bolus arrival time, time of maximum blackening, etc.); (4) identifying vascular voxels that are contrast-enhanced in both (or more) angiographic 4D images; and/or (5) temporally synchronizing the 4D images (also referred to here as 4D reconstructions) on the basis of these common vascular voxels. The bolus arrival time (or other temporal measure, for example, time of maximum blackening) defines the "anchor time" for temporal synchronization.

FIG. 1 shows a workflow illustrating the spatiotemporal fusion of two angiographic 4D data sets or 4D reconstructions 1 and 2. The first 4D reconstruction was obtained from a first time-resolved angiographic 3D data set of a patient who has received an initial contrast administration at a first site. The second 4D reconstruction is obtained from a second time-resolved angiographic 3D data set of the patient who has received a second contrast administration at a second site different from the first.

In FIG. 1, 4D reconstructions 1 and 2 are shown in two dimensions. In the case of a first administration of contrast agent, on which the first 4D reconstruction 1 is based, the contrast agent was injected into a first artery 3. From this first artery 3, the contrast agent flows into a first section 4 of a vascular tangle 5.

The selected representation of the first 4D reconstruction 1 shows the temporal dynamics of the contrast agent within the vascular structure. Accordingly, the contrast agent reaches the first artery 3 about 150 ms after injection. After about 200 to 300 ms, finer vascular structures 6 are reached. After about 400 ms, the contrast agent is carried away in venous outflows 7.

Similarly, the second 4D reconstruction 2 is based on contrast agent administration into a second artery 8. From this second artery 8, the blood or contrast agent flows into finer vascular structures 9 before it is again discharged in venous outflows 10. The time scale again indicates when the contrast agent reaches the corresponding areas.

Because the vascular tangle 5 has numerous arteriovenous malformations and shunts, contrast agent from the first artery 3 flows into the same vascular region as contrast agent from the second artery 8. This vascular region may be referred to as the common vascular region 11. Thus, in this common vascular region 11, the contrast agent enters both the first artery 3 during the first contrast agent administration and the second artery 8 during the second contrast agent administration. For this reason, this common vascular region 11 is shown in both 4D reconstructions 1 and 2.

Because the common region 11 is rendered in both 4D reconstructions 1 and 2, the two 4D reconstructions 1 and 2 may be spatially registered to each other. This means that the two 4D reconstructions 1 and 2 are spatially aligned and displayed together. Such spatial registration results in the spatially registered image 12, which shows the vascular regions of the first 4D reconstruction 1 and the second 4D reconstruction 2 in different colors. Vascular regions affected by both contrast agent administrations appear in a color-mixed manner (for example, purple if the vascular structures of the first contrast agent administration are colored red and the vascular structures of the second contrast agent administration are colored blue).

Finally, temporal registration of the two 4D reconstructions 1 and 2 is performed, resulting in the temporal registration image 13 which represents a fusion of the two synchronized 4D reconstructions 1 and 2 in simplified form. In the temporal registration image 13, as in the spatial registration image 12, all vessel sections of the two contrast agent administrations or of the two 4D reconstructions 1 and 2, may be identified. In the fused 4D data set, however, the contrast agent flows are now also synchronized, e.g., time-aligned. In this case, the time-point at which the contrast agent arrives in the common region 11 was determined as the synchronization time. The fusion thus results in a three-dimensional video recording which is based on two three-dimensional video recordings that have been spatially and temporally registered to each other.

Figure 2:
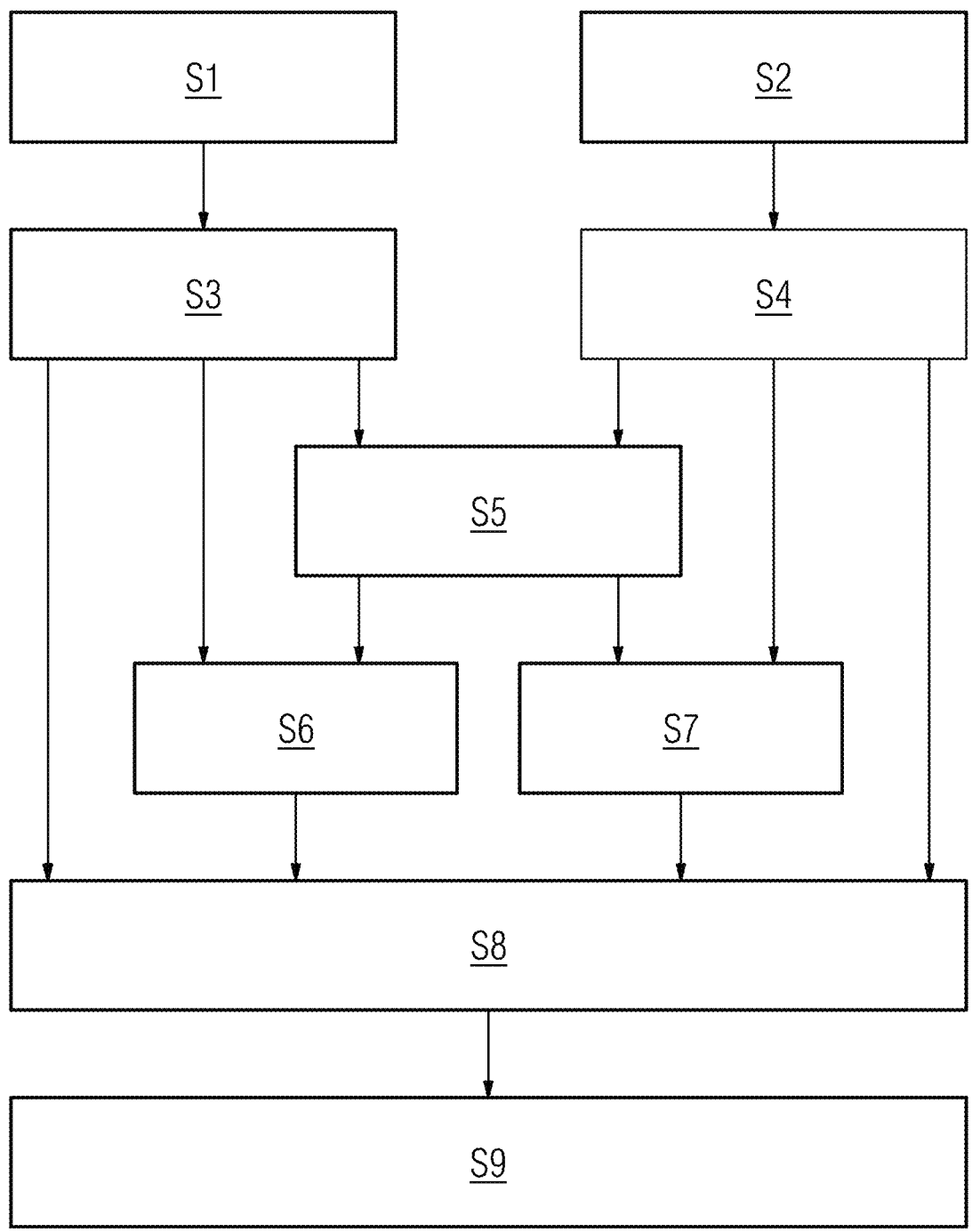
FIG. 2 depicts a schematic block diagram of an exemplary embodiment of a method.

FIG. 2 is a flowchart showing the more detailed sequence of an example of a method for spatiotemporal fusion of time-resolved angiographic data sets. In act S1, a first time-resolved angiographic 3D data set of a patient is provided or acquired or recorded. For this purpose, the patient has received a first contrast agent administration at a first site. In act S2, a second time-resolved angiographic 3D data set of the patient is provided or acquired or recorded, wherein the patient has received for this purpose a second administration of contrast agent at a second site different from the first site.

In act S3, a first 4D reconstruction is obtained from the first time-resolved angiographic 3D data set. Similarly, in act S4, a second 4D reconstruction or a second 4D data set, is obtained from the second time-resolved angiographic 3D data set.

In act S5, a common vascular region represented by the two 4D reconstructions or data sets is determined. This common vascular region of the patient is important for the subsequent spatial and temporal registration of the 4D data sets to each other. For this purpose, in act S6, a first time point or time course relating to an appearance of a first contrast agent bolus of the first contrast agent administration in the common vascular region is determined from the first 4D reconstruction. Similarly, a second time or time course concerning an appearance of a second contrast agent bolus of the second contrast agent administration in the common vascular region is determined from the second 4D reconstruction.

In act S8, the two 4D data sets, i.e., the first 4D reconstruction and the second 4D reconstruction, are synchronized based on the first and second time points or time courses. Finally, in act S9, the two synchronized 4D reconstructions are fused. In this way, for example, two synchronized 3D video recordings are obtained in a common representation.

Figure 3:
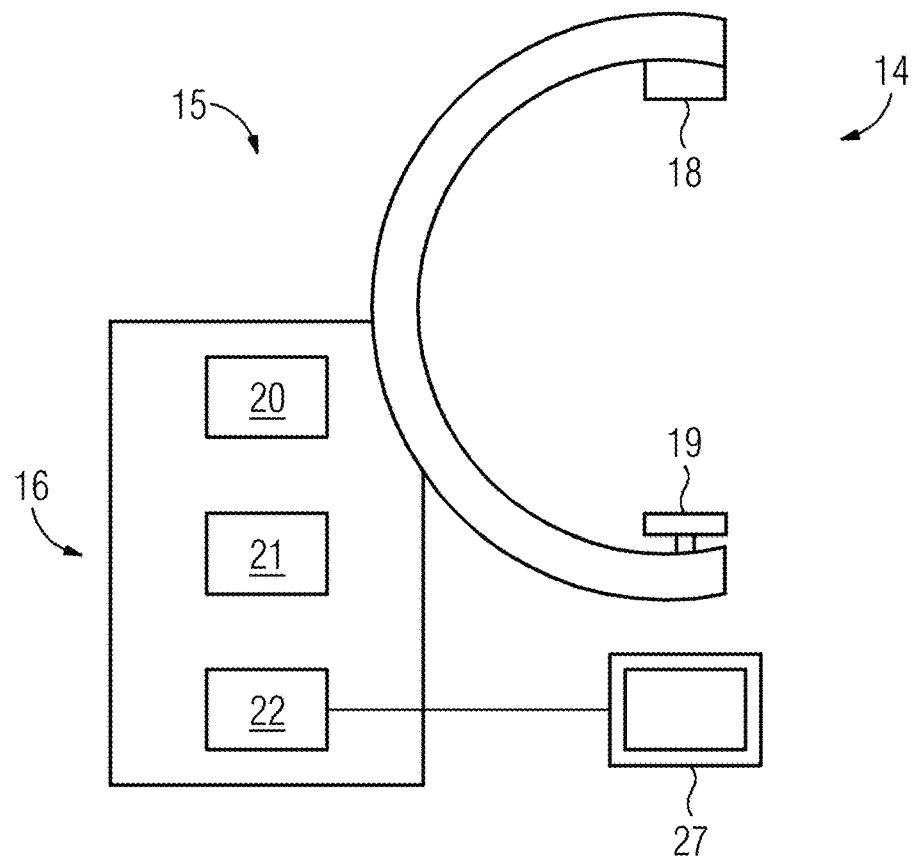
FIG. 3 schematically illustrates an example of an angiography apparatus.

FIG. 3 schematically illustrates an exemplary embodiment of an angiography apparatus 14 that includes an angiography unit 15 and an image processing unit 16. The angiography unit may have a C-arm 17 with an X-ray emitter 18 and an opposite X-ray detector 19. The angiography unit 15 may also have a control unit 20 for controlling the recording operation for obtaining/capturing corresponding time-resolved 3D angiographic data sets as required. The angiography apparatus optionally has a storage unit 21 for storing the acquired time-resolved angiographic 3D data sets and making them available for subsequent image processing.

If necessary, the image processing unit 16 of the angiography apparatus 14 may also be implemented as an independent apparatus having a memory unit 21 and/or a data interface with which corresponding 3D data sets may be provided. In addition, the image processing unit 16 may have a computing unit 22 with which the 4D reconstructions or 4D data sets are obtained from the 3D data sets. The computing unit 22 may also be used to determine a common vascular region and a first time point or time course of the first contrast agent bolus and a second time point or time course of the second contrast agent bolus in the common vascular region. Lastly, the computing unit 22 is also designed to synchronize the two 4D reconstructions based on the time points or time courses and to fuse the two synchronized 4D reconstructions and display them on a screen 27 as required.

Some details are described below with which the methods and apparatuses described may be further developed or which should be noted where appropriate. The common vascular area may be characterized by a vascular voxel or region of vascular voxels and may be on the venous or arterial side, depending on the two injection sites and the patient's vascular pathology. An early enhanced shared voxel (or region of shared vascular voxels) may be used for temporal registration in order to minimize inaccuracies, because, in the case of later enhanced voxels, the contrast enhancement is attenuated due to the cross-flow of non-contrast-enhanced blood as well as dispersion of the bolus.

The two (or more) angiographic 4D data sets are already spatially registered because they are mainly acquired during the same procedure and the patient does not move much, if at all, between acquisitions. However, if necessary, one or more spatial registrations are performed prior to temporal registration or synchronization. Approaches for spatial registration are known from the prior art.

In a particular embodiment, as indicated above, more than two 4D angiography data sets may be appropriately fused. In another embodiment, at least two 4D angiographic data sets are fused with at least one 3D angiographic data set (for example, a static CTA or MRA image). In another embodiment, at least two angiographic 4D data sets are fused with at least one tomographic 3D data set (for example, a static CT or MR image).

The method may be used for vascular pathologies outside and inside the brain. For example, the method may also be used to analyze peripheral AVMs in the extremities or face.

Figure 4:
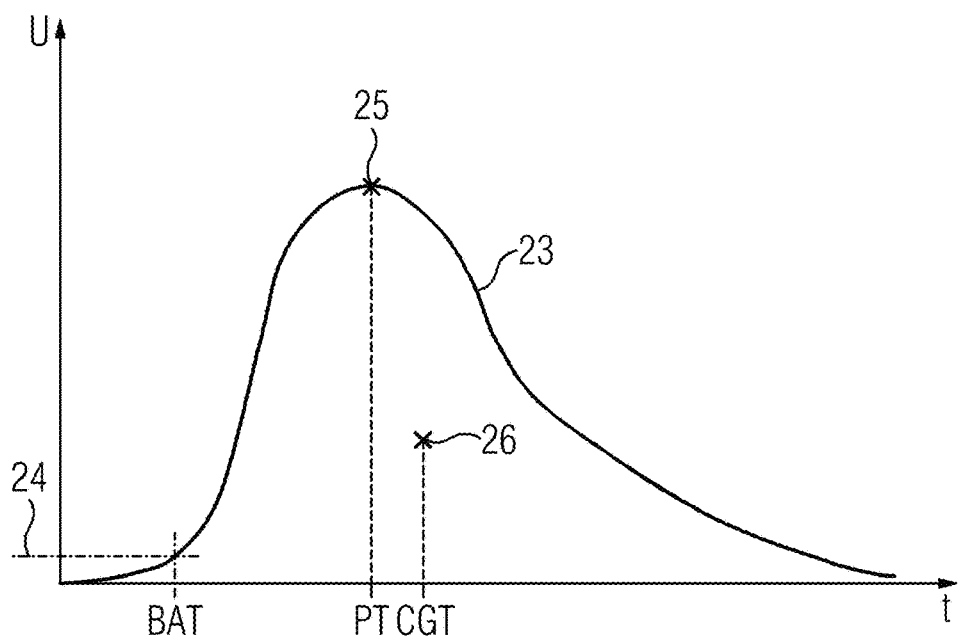
FIG. 4 depicts an example of a time course, i.e., a time-contrast curve of a contrast agent in a vessel (vascular region).

In further exemplary embodiments, the time parameters used to temporally synchronize the two or more 4D angiography data sets may be varied. These possible variations may be seen in FIG. 4, which shows the contrast agent concentration time course, i.e., a time-contrast curve, in a vessel. Where appropriate, only part of the time-contrast curve is used for synchronization. The X-ray agent concentration may be proportional to the X-ray attenuation or absorption coefficient $\mu$. The contrast agent is administered, for example, at time t=0. At a given location in the vascular tree, a wash-in phase then occurs. The blackening or the absorption coefficient, reaches a threshold value 24 at a time BAT (bolus arrival time). This threshold value 24 is, for example, the detection threshold. This means that the contrast agent may only be detected at all unambiguously from the detection threshold value 24 onwards. Subsequently to the bolus arrival time BAT, the contrast agent concentration and thus the absorption coefficient $\mu$ increases according to the time course 23 up to a maximum or peak 25. This peak 25 is reached at a peak time PT. Subsequently, the absorption coefficient at the particular vessel site decreases continuously again. The overall time course 23 of the contrast agent concentration has a center of gravity 26, which is characterized by a center of gravity time CGT.

This provides a number of time parameters that may be used for temporal synchronization of the two or more 4D angiography data sets, namely relating to two or more contrast agent administrations: corresponding bolus arrival times BAT, corresponding peak times PT at maximum contrast agent concentration, corresponding time points CGT of the centers of gravity of the respective time-contrast curves 23, selection of the synchronization time point at which the normalized cross-correlation of the time-contrast curves 23 becomes maximal, or other time parameters resulting from the time-contrast curves 23 may also be used for synchronization.

The exemplary embodiments disclosed above are based on the approach of generating combined 4D vessel representations based on a plurality of 4D recordings with different contrast injection sites. This may produce a more complete image of the entire vasculature supplying an organ (for example, the brain) or vascular disease (for example, an AVM). In the case of an AVM intervention, such spatiotemporally fused 4D image of this kind may be used to plan all possible arterial and venous embolization routes based on a common data set.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for spatiotemporal fusion of time-resolved angiographic data sets, the method comprising:
   providing a first time-resolved angiographic three-dimensional (3D) data set of a patient who has received a first contrast agent administration at a first site;
   providing a second time-resolved angiographic 3D data set of the patient who has received a second contrast agent administration at a second site different from the first site;
   obtaining a first four-dimensional (4D) reconstruction from the first time-resolved angiographic 3D data set;
   obtaining a second 4D reconstruction from the second time-resolved angiographic 3D data set;
   determining a common vascular region represented by both the first 4D reconstruction and the second 4D reconstruction of the patient;
   determining, from the first 4D reconstruction, a first time point or first time course relating to an appearance of a first contrast agent bolus of the first contrast agent administration in the common vascular region;
   determining, from the second 4D reconstruction, a second time point or second time course relating to an appearance of a second contrast agent bolus of the second contrast agent administration in the common vascular region;
   synchronizing the first 4D reconstruction and the second 4D reconstruction based on the first time point and the second time point or the first time course and the second time course; and
   fusing the synchronized 4D reconstructions.

2. The method of claim 1, wherein the first time point corresponds to a time of arrival of the first contrast agent bolus in the common vascular region, and wherein the second time point corresponds to a time of arrival of the second contrast agent bolus in the common vascular region.

3. The method of claim 1, wherein the first time point corresponds to a time point of maximum concentration of the first contrast agent bolus in the common vascular region, and
wherein the second time point corresponds to a time point of maximum concentration of the second contrast agent bolus in the common vascular region.

4. The method as claimed in claim 1, wherein the first time point corresponds to a time when a center of gravity of the first contrast agent bolus is in the common vascular region, and
wherein the second time point corresponds to a time when a center of gravity of the second contrast agent bolus is in the common vascular region.

5. The method of claim 1, wherein a time point of maximum cross-correlation of the first time course and the second time course is used for the synchronizing.

6. The method of claim 5, wherein a plurality of vascular regions is determined from the first 4D reconstruction and the second 4D reconstruction into which both the first contrast agent bolus and the second contrast agent bolus flow, and
wherein the vascular region reached first by the respective contrast agent bolus of the two contrast agent administrations is automatically determined as the common vascular region.

7. The method of claim 6, wherein at least one further 4D reconstruction is synchronized and fused with the first 4D reconstruction and the second 4D reconstruction.

8. The method of claim 5, wherein at least one further 4D reconstruction is synchronized and fused with the first 4D reconstruction and the second 4D reconstruction.

9. The method of claim 5, wherein the first 4D reconstruction and the second 4D reconstruction are fused with a 3D angiographic data set.

10. The method of claim 5, wherein the first 4D reconstruction and the second 4D reconstruction are fused with a 3D tomographic data set.

11. The method of claim 1, wherein a plurality of vascular regions is determined from the first 4D reconstruction and the second 4D reconstruction into which both the first contrast agent bolus and the second contrast agent bolus flow, and
wherein the vascular region reached first by the respective contrast agent bolus of the two contrast agent administrations is automatically determined as the common vascular region.

12. The method of claim 11, wherein at least one further 4D reconstruction is synchronized and fused with the first 4D reconstruction and the second 4D reconstruction.

13. The method of claim 1, wherein at least one further 4D reconstruction is synchronized and fused with the first 4D reconstruction and the second 4D reconstruction.

14. The method of claim 1, wherein the first 4D reconstruction and the second 4D reconstruction are fused with a 3D angiographic data set.

15. The method of claim 1, wherein the first 4D reconstruction and the second 4D reconstruction are fused with a 3D tomographic data set.

16. An image processing apparatus for spatiotemporal fusion of time-resolved angiographic data sets, the image processing apparatus comprising:
a storage unit configured to:
provide a first time-resolved angiographic three-dimensional (3D) data set in a patient who has received a first contrast agent administration at a first site; and
provide a second time-resolved angiographic 3D data set at the patient who has received a second contrast agent administration at a second site different from the first site; and
an image processing unit configured to:
obtain a first four-dimensional (4D) reconstruction from the first time-resolved angiographic 3D data set;
obtain a second 4D reconstruction from the second time-resolved angiographic 3D data set;
determine a common vascular region represented by both the first 4D reconstruction and the second 4D reconstruction of the patient;
determine, from the first 4D reconstruction, a first time point or first time course relating to an appearance of a first contrast agent bolus of the first contrast agent administration in the common vascular region;
determine, from the second 4D reconstruction, a second time point or second time course relating to an appearance of a second contrast agent bolus of the second contrast agent administration in the common vascular region;
synchronize the first 4D reconstruction and the second 4D reconstruction based on the first time point and the second time point or the first time course and the second time course; and
fuse the synchronized 4D reconstructions.

17. An angiography apparatus for spatiotemporal fusion of time-resolved angiographic data sets, the angiography apparatus comprising:
an angiography unit configured to:
acquire a first time-resolved angiographic three-dimensional (3D) data set for a patient who has received a first contrast agent administration at a first site; and
acquire a second time-resolved angiographic 3D data set for the patient who has received a second contrast agent administration at a second site different from the first site; and
an image processing unit configured to:
obtain a first four-dimensional (4D) reconstruction from the first time-resolved angiographic 3D data set;
obtain a second 4D reconstruction from the second time-resolved angiographic 3D data set;
determine a common vascular region represented by both the first 4D reconstruction and the second 4D reconstruction of the patient;
determine, from the first 4D reconstruction, a first time point or first time course relating to an appearance of a first contrast agent bolus of the first contrast agent administration in the common vascular region;
determine, from the second 4D reconstruction, a second time point or second time course relating to an appearance of a second contrast agent bolus of the second contrast agent administration in the common vascular region;
synchronize the first 4D reconstruction and the second 4D reconstruction based on the first time point and the second time point or the first time course and the second time course; and
fuse the synchronized 4D reconstructions.

* * * * *